United States Patent
Sedai et al.

(10) Patent No.: US 10,832,074 B2
(45) Date of Patent: Nov. 10, 2020

(54) UNCERTAINTY REGION BASED IMAGE ENHANCEMENT

(71) Applicant: International Business Machines Corporation, Armonk, NY (US)

(72) Inventors: Suman Sedai, Hughesdale (AU); Bhavna Josephine Antony, Brunswick East (AU); Kerry Halupka, Northcote (AU); Dwarikanath Mahapatra, Melbourne (AU); Rahil Garnavi, Macleod (AU)

(73) Assignee: INTERNATIONAL BUSINESS MACHINES CORPORATION, Armonk, NY (US)

( * ) Notice: Subject to any disclaimer, the term of this patent is extended or adjusted under 35 U.S.C. 154(b) by 54 days.

(21) Appl. No.: 16/296,593

(22) Filed: Mar. 8, 2019

(65) Prior Publication Data
US 2020/0285880 A1 Sep. 10, 2020

(51) Int. Cl.
*G06K 9/00* (2006.01)
*G06K 9/32* (2006.01)
(Continued)

(52) U.S. Cl.
CPC .......... *G06K 9/3233* (2013.01); *A61B 5/0066* (2013.01); *G06T 5/002* (2013.01); *G06T 7/0012* (2013.01)

(58) Field of Classification Search
CPC .......... G06T 7/337; G06T 7/30; G06T 7/248; G06T 7/0012; G06T 7/0014; G06T 7/20; G06T 2207/10116; G06T 2207/10124; G06T 7/11; G06T 7/174; G06T 7/0016; G06T 7/0028; G06T 5/002; A61B 6/5235;
(Continued)

(56) References Cited

U.S. PATENT DOCUMENTS 8,194,936 B2 * 6/2012 Abramoff .......... G06K 9/00617
382/275
8,861,817 B2 10/2014 Imamura et al.
(Continued)

FOREIGN PATENT DOCUMENTS

WO 2006116672 A2 11/2006

OTHER PUBLICATIONS

Saba Adabi et al., "A Learnable Despeckling Framework for Optical Coherence Tomography Images".

*Primary Examiner* — Duy M Dang
(74) *Attorney, Agent, or Firm* — Garg Law Firm, PLLC; Rakesh Garg; Joseph Petrokaitis

(57) ABSTRACT

From a first image using a model, a first uncertainty map is generated. An uncertainty level of a location in the first uncertainty map corresponds to a detection of a known structure in a portion of the first image. A first weighted image corresponding to the first uncertainty map is generated, the generating including assigning a first weight to a pixel of the first image, the first weight corresponding to the uncertainty level of a location in the first uncertainty map corresponding to the pixel. From a second image using a model, a second uncertainty map is generated. A second weighted image corresponding to the second uncertainty map is generated. The first image and the second image are combined to form a composite image, each image participating in the composite image according to the corresponding weighted image.

20 Claims, 9 Drawing Sheets

(51) Int. Cl.
*G06T 7/00* (2017.01)
*G06T 5/00* (2006.01)
*A61B 5/00* (2006.01)

(58) Field of Classification Search
CPC ... A61B 6/5229; A61B 6/5247; A61B 6/5258; A61B 6/585; A61B 6/032; A61B 6/4258; A61B 6/5223; A61B 6/5264; A61B 6/469; A61B 6/503; A61B 6/504; A61B 6/5217; A61B 5/0066; G06K 9/0053; G06K 9/4609; G06K 9/6202; G06K 9/20; G06K 9/00208; G06K 9/4642; G06K 9/3233

See application file for complete search history.

(56) References Cited

U.S. PATENT DOCUMENTS

| | | |
|---|---|---|
| 9,250,060 B2 | 2/2016 | Kang et al. |
| 2013/0321819 A1 | 12/2013 | Lim et al. |
| 2015/0327761 A1 | 11/2015 | Narasimha-Iyer et al. |
| 2017/0238877 A1 | 8/2017 | Hsiao et al. |
| 2017/0345134 A1* | 11/2017 | Cresens .................. G06T 5/005 |
| 2018/0042473 A1 | 2/2018 | Wang et al. |
| 2019/0313963 A1* | 10/2019 | Hillen .................. G06N 3/0454 |
| 2020/0027218 A1* | 1/2020 | Buibas ................ G06K 9/00771 |

* cited by examiner

UNCERTAINTY REGION BASED IMAGE ENHANCEMENT

TECHNICAL FIELD

The present invention relates generally to a method, system, and computer program product for image enhancement. More particularly, the present invention relates to a method, system, and computer program product for uncertainty region based image enhancement.

BACKGROUND

Images of subjects having a known structure are an important class of image data. This type of image data is common in medical imaging. For example, optical coherence tomography (OCT) is an imaging technique that uses low-coherence light to capture micrometer-resolution, two- and three-dimensional sub-surface images of translucent or opaque materials (e.g. biological tissue), without sample preparation or ionizing radiation. In OCT, light is reflected onto the subject matter being studied and an image formed of the light reflected back. Although OCT is also used in non-biological applications—for example, art conservation and other non-destructive testing applications—OCT is commonly used to obtain images of the retina portion of an eye. Covering the inside of most of the eye, the retina is a multilayered structure responsible for transforming light energy into neural signals for further use by the brain. OCT typically results in two-dimensional grey-scale images including a cross-sectional view and topographic view of the retina, where subtle differences in retinal structure are shown by different pixel brightness levels caused by differences in the light levels reflected back to a light sensor. The images can be used in diagnosis and management of eye diseases such as glaucoma and macular degeneration.

As another example, medical ultrasound (also known as sonography) is a diagnostic imaging technique based on the application of ultrasound. Similar to OCT, in sonography a pulse of sound is reflected onto the subject matter being studied and an image formed based on the sound reflected back. For example, a B-mode or brightness image displays the acoustic impedance of a two-dimensional cross-section of tissue. Other types of medical ultrasound imaging can display blood flow, motion of tissue over time, the location of blood, the presence of specific molecules, the stiffness of tissue, or the anatomy of a three-dimensional region.

As well, magnetic resonance imaging (MRI) is another diagnostic imaging technique uses a large magnet, radio waves, and a computer to create a detailed, cross-sectional image of known anatomical structures. X-ray imaging uses electromagnetic radiation in the x-ray frequency range to image anatomical structures such as bones. Other medical imaging modalities also image known structures, for use in diagnosis and other medical applications.

Images of subjects having a known structure are also important in areas beyond medical imaging. For example, satellite imagery of subjects on the ground having a known structure, non-destructive materials testing and other material science applications, and other monitoring applications using common photography all are concerned with imaging subjects having a known structure as well.

SUMMARY

The illustrative embodiments provide a method, system, and computer program product. An embodiment includes a method that generates, from a first image using a model, a first uncertainty map, wherein an uncertainty level of a location in the first uncertainty map corresponds to a detection of a known structure in a portion of the first image. An embodiment generates, corresponding to the first uncertainty map, a first weighted image, the generating comprising assigning a first weight to a pixel of the first image, the first weight corresponding to the uncertainty level of a location in the first uncertainty map corresponding to the pixel. An embodiment generates, from a second image using the model, a second uncertainty map, wherein an uncertainty level of a location in the second uncertainty map corresponds to a detection of a known structure in a portion of the second image. An embodiment generates, corresponding to the second uncertainty map, a second weighted image, the generating comprising assigning a second weight to a pixel of the second image, the second weight corresponding to the uncertainty level of a location in the second uncertainty map corresponding to the pixel. An embodiment combines the first image and the second image to form a composite image, the first image participating in the composite image according to the first weighted image and the second image participating in the composite image according to the second weighted image.

An embodiment includes a computer usable program product. The computer usable program product includes one or more computer-readable storage devices, and program instructions stored on at least one of the one or more storage devices.

An embodiment includes a computer system. The computer system includes one or more processors, one or more computer-readable memories, and one or more computer-readable storage devices, and program instructions stored on at least one of the one or more storage devices for execution by at least one of the one or more processors via at least one of the one or more memories.

BRIEF DESCRIPTION OF THE DRAWINGS

Certain novel features believed characteristic of the invention are set forth in the appended claims. The invention itself, however, as well as a preferred mode of use, further objectives and advantages thereof, will best be understood by reference to the following detailed description of the illustrative embodiments when read in conjunction with the accompanying drawings, wherein:

DETAILED DESCRIPTION

Figure 1:
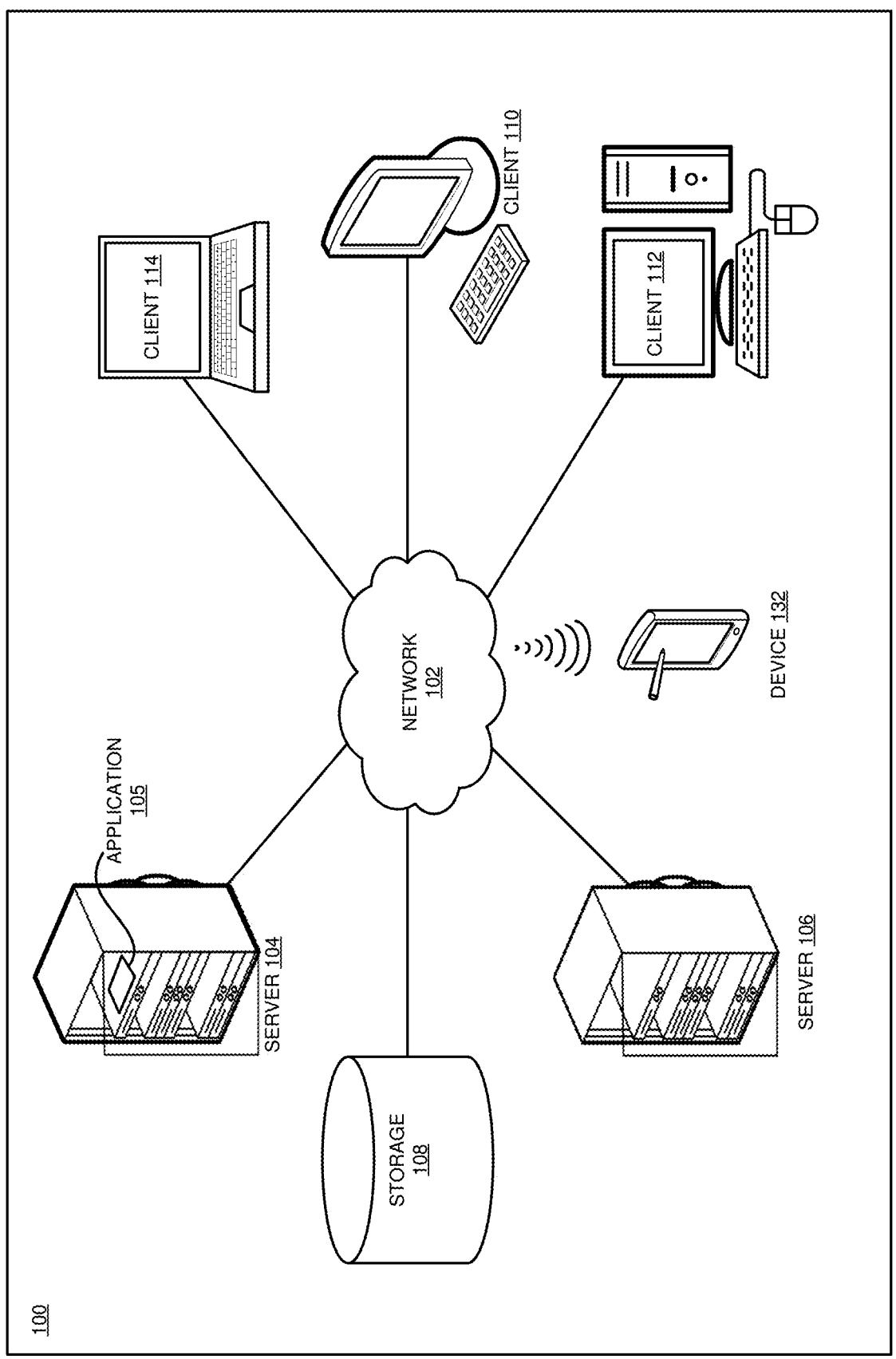
FIG. 1 depicts a block diagram of a network of data processing systems in which illustrative embodiments may be implemented.

The illustrative embodiments recognize that image data of subjects having a known structure—for example, resulting from OCT, sonography, or another imaging technique—is subject to two types of errors: speckle noise (i.e. random granular noise) and interference from another object between the camera and the subject being imaged. Both types of errors degrade the image quality, mask image features, and make it difficult to use the images to perform the task for which the images were captured. For example, lack of clarity at the edges of a particular structure being imaged can make it difficult to perform a reliable size measurement of that structure, or to diagnose a medical problem with that structure.

Speckle causes the grainy appearance of images such as those obtained from OCT and sonography, and is dependent on both the wavelength of the imaging beam and the structural characteristics of the subject of the imaging. Therefore, speckle contains both noise and information, and the two must be separated to improve image quality.

In addition, in some applications, the subject of the imaging may move, or intervening structures may lie between the image sensor and a portion of the subject of the imaging, causing undesirable imaging artifacts. For example, when imaging a retina of an eye, a small eye movement, called a microsaccade, may occur, or the patient may blink the eye being imaged. Such small movements can create transient artifacts, present in one image but not another. In addition, a translucency or an opacity—for example, caused by a cataract—may lie between the image sensor and the retina being imaged, preventing or degrading any image of the area shadowed by the opacity.

The illustrative embodiments recognize that current methods attempt to reducing speckle noise, without considering the effects of artifacts. One prior art implementation collects multiple images of the same location and averages the images together to reduce speckle noise. Another prior art implementation refines the method by averaging multiple images together several times, until the signal to noise ratio of the averaged image reaches a threshold level (i.e. the noise has been sufficiently reduced). In another refinement, particularly poor quality images are manually evaluated and discarded, and only the better quality images are averaged together. However, such methods require additional patient time while the need for additional images is evaluated and necessary additional images are obtained, manual intervention with associated subjectivity to evaluate and discard poor quality images, and the lack of a consistent relationship between the number of images needed and the quality of those images. In addition, such manual intervention requires clinical or other specialized skill training. As a result of this lack, healthy subjects may be overimaged, obtaining additional unneeded images of already-acceptable quality, while failing to obtain enough images to produce a result of acceptable quality in less healthy subjects.

Consequently, the illustrative embodiments recognized that what is needed in the art is a method that improves image quality using fewer images than previously required. In addition, the method should produce a quality metric after each image quality update to tie a need for additional imaging to the current quality level. Further, the method should not require manual intervention to discard poor quality images.

The illustrative embodiments recognize that the presently available tools or solutions do not address these needs or provide adequate solutions for these needs. The illustrative embodiments used to describe the invention generally address and solve the above-described problems and other problems related to uncertainty region based image enhancement.

An embodiment can be implemented as a software application. The application implementing an embodiment can be configured as a modification of an existing imaging system, as a separate application that operates in conjunction with an existing imaging system, a standalone application, or some combination thereof.

Particularly, some illustrative embodiments provide a method by which pixels of an image within a set of images are weighted according to an uncertainty level associated with recognizing known structure within the images. Then, the images are combined to create a composite image based on the uncertainty levels.

An embodiment is configured to process images that include a particular known structure. For example, in an embodiment configured for enhancing OCT images of retinas, the embodiment is configured to process images that include a retina.

An embodiment receives images from which to create an enhanced image. Each of the images are of the same subject, which has a known structure the embodiment is configured to process. For example, in an embodiment configured for enhancing OCT images of retinas, each image is of the same eye of the same patient. Each of the images may have been taken at different times, from different angles or perspectives, using different methods, or using different equipment or equipment settings, but the embodiment processes the images assuming that each contains a particular known structure, such as retina.

An embodiment uses a prior-art registration process to register the received images. The registration process adjusts each image to conform to the alignment and size of a reference image of the known structure the embodiment is configured to process. For example, in an embodiment configured for enhancing OCT images of retinas, the reference image is an image of a retina. Registering each image to a common reference ensures that the same coordinates in each image depict the same areas of known structure. As a result, during a later image composition process, pixels of different images being composited are located in the same relative position with respect to known structure within the subject of the images.

In particular, if the received image is larger or smaller than the reference image, the received image is rescaled to match the reference image. If the received image is rotated with respect to the reference image, the received image is rotated to match the reference image. If the received image was taken from a point of view different from that of the reference image, the registration process performs a perspective transformation on the received image to match that of the reference image. If the received image was captured using a different intensity scale, or using a different color palette, from that of the reference image, the registration process converts the intensity scale or color palette of the received image to match that of the reference image. If the received image has a different depth of field from that of the reference image, the registration process adjusts the depth of field of the received image to match that of the reference image. The registration process also performs additional adjustments to the received image to ensure image alignment and sizing consistent with the reference image.

To create an enhanced image from the received images, an embodiment uses a model. The model identifies, within an image, the known structure the embodiment is configured to process. The model can be implemented using a neural network. For example, in one embodiment configured to enhance OCT images of retinas, the model is a fully convolutional neural network trained to segment OCT images. The embodiment uses an existing, already-trained model, and does not perform additional model training. Other model implementations, using other machine learning and image recognition techniques, are also possible and contemplated within the scope of the illustrative embodiments. For example, other neural network configurations, a random forest technique, and gaussian process classification can be used to replace corresponding functions described in the example embodiment without departing the scope of the illustrative embodiments.

For each image to be used in creating the enhanced image, an embodiment uses the model to compute a corresponding uncertainty map. When the model identifies known structure at a location within an image, the model also produces a level of uncertainty associated with that identification at that location. The level of uncertainty may vary, due to noise and occlusion effects on the image. For example, if an area of the subject being imaged is occluded or noisy, the model may have more difficulty identifying known structure in that area than for another, less occluded or less noisy, area. This difficulty is expressed as a level of uncertainty. The level of uncertainty is a number within a range, where the low end of the range (e.g. 0 percent) denotes a very low uncertainty (i.e. a very high confidence) in the model's identification, and the high end of the range (e.g. 100 percent) denotes a very high uncertainty (i.e. a very low confidence) in the model's identification.

An uncertainty map maps these levels of uncertainty into a two-dimensional format, with a pixel of the uncertainty map having coordinates corresponding to an area within the image. A pixel of the uncertainty map has, as a value, the model's level of uncertainty for the corresponding image area. Thus, for example, if the model produced a 50 percent level of uncertainty associated with its identification of known structure at the top left corner of an image, the corresponding uncertainty map would have a pixel with a value of 50 percent at coordinates corresponding to the top left corner of the image.

In a non-limiting example, an embodiment is configured for enhancing OCT images of retinas using a fully convolutional neural network trained to identify retinal layers at a location within an image as the model. The neural network also produces a level of uncertainty associated with the retinal layer identification. Multiple test iterations are used to determine an uncertainty value for a region of an image. For each iteration, a network output, or prediction, is obtained by dropping a subset of the trained network weights to an ignorable level. The variance of the outputs over multiple test iterations determines an uncertainty level in the known structure identification for that region of the image, and the mean of the outputs is used as as the final prediction of the structure in the image. In particular, if $y_1, y_2 \ldots y_T$ are T predictions made by the network then the prediction is computed as $$\mu = 1/T \sum_{i=1}^{T} y_i$$

and the uncertainty is computed as $$U = 1/T \sum_{i=1}^{T} (\mu - y_i)^2.$$

An embodiment can repeat the process, removing a different portion of the network weights on each test iteration. An embodiment can select portion of network weights for removal using any suitable pattern. For example, an embodiment can divide the network weights into a predetermined number of adjacent portions, then select a portion using a number obtained by a pseudorandom number generation function of an application implementation. As another example, an embodiment can iterate through each adjacent portion in order. Other portion removal techniques are also possible and contemplated within the scope of the illustrative embodiments. The variance of the outputs from the multiple test iterations determines an uncertainty level in the known structure identification for that region of the image.

An embodiment normalizes each uncertainty value within each uncertainty map to a common uncertainty range using a soft-max activation function. A soft-max activation function takes as input a set of values, some of which may be outside the range from 0-1. In addition, the input set of values may not sum to 1. The soft-max activation function converts this input set of values to a corresponding set of output values, all of which are in the 0-1 range. In addition, the sum of the output values is 1. An example of a soft-max activation function is $$w_i = \frac{\exp(x_i)}{\sum_{j=1}^{N} \exp(x_j)},$$

where N is the total number of input values and $x_i$ is an input value. An exponential function need not be used; instead, any non-zero base greater than zero can be substituted for the exponential function. Normalizing the uncertainty values within each uncertainty map in this fashion ensures that each uncertainty map uses the same uncertainty scale and range. Normalizing the uncertainty values in this manner allows direct comparison of uncertainty maps. Other output adjustment schemes are also possible and contemplated within the scope of the illustrative embodiments.

An embodiment uses the uncertainty map corresponding to an image to compute a confidence weight. The confidence weight is inversely related to the uncertainty level of a region of the image. This process of confidence weighting results in a weighted image.

In particular, one embodiment converts an uncertainty level within an uncertainty map to a confidence weight using a suitable function. One non-limiting example of such a function is an inverse softmax function. In other words, the confidence weight of one pixel in the $i^{th}$ image is $$w_i = \frac{\exp(-U_i)}{\sum_{j=1}^{N} \exp(-U_j)},$$

where N is the total number of images being processed and $U_j$ is the uncertainty value for the corresponding pixel in the $i^{th}$ image. Thus, a higher weight is assigned to a pixel corresponding to a lower uncertainty value, and a lower weight is assigned to a pixel corresponding to a higher uncertainty value. In addition, in an embodiment all the weights assigned to a particular pixel, across all images being composited, sum to a fixed value, e.g., 1. Other weight values, using a different range, different fixed value, or some combination thereof, are also possible and contemplated within the scope of the illustrative embodiments.

An embodiment adjusts weights of one or more weighted images. In particular, to enhance only a portion of the weighted images, an embodiment sets the weight of image pixels outside the portion or region of interest to below an ignorable weight threshold, e.g., to zero.

An embodiment combines at least two weighted images to create a composite image. One embodiment creates a composite image by computing a weighted average of corresponding pixels in each weighted image. Because the weighted images have been weighted according to uncertainty maps of each image, the composite image will include the least uncertain, or most certain, regions of each of the original images—thus combining the best parts of each source image.

In addition, one or more pixel weights may have been previously set to below an ignorable weight threshold to exclude an area outside a region of interest. Pixels below the ignorable weight threshold will not contribute to the resulting composite image. As a result, only the image portion inside the region of interest will be enhanced.

An embodiment computes an enhancement metric corresponding to the composite image. An enhancement metric corresponding to the composite image is a measure of the degree to which the composite image has been enhanced, or improved, compared to an input image. In particular, an embodiment averages together uncertainty maps used to create the composite image. Then, in one embodiment, if at least a threshold number of pixels or regions in the resulting average uncertainty map are below a predetermined threshold, or at least a threshold number of pixels or regions of a portion of the average uncertainty map corresponding to a region of interest is below a predetermined threshold, the composite image is deemed to be sufficiently enhanced, and image processing may stop. The threshold number of pixels or regions can be, but need not necessarily be, all pixels, or all regions that are being considered in the processing.

Another embodiment computes the enhancement metric R=1−(number of pixels with uncertainty value>T in a region of interest)/(total number of pixels in the region), where T is a predetermined threshold, for a region of or the entire average uncertainty map. If the value of the resulting enhancement metric R is above a predetermined threshold, the embodiment deems the composite image to be sufficiently enhanced, and image processing may stop.

If the enhancement metric value is not above a threshold, meaning that the composite image is not sufficiently improved, an embodiment repeats the process of obtaining and registering an additional image, computing an uncertainty map corresponding to the additional image, computing a weighted image corresponding to the uncertainty map, and computing a new composite image from a set of weighted images including the new weighted image. If the new composite image has an enhancement metric value above a threshold, the process stops; otherwise the embodiment iterates, processing an additional image in a manner described herein until a composite image with a sufficient enhancement metric value is produced or a maximum number of iterations is reached. The additional image may have been obtained at the same time as the previously-processed images, or obtained later. A sufficient enhancement metric value and a maximum number of iterations can be determined in cooperation with end users of particular types of images, to ensure that resulting composite images meet users' needs without requiring unrealistic numbers of images and associated imaging time and resources.

The manner of uncertainty region based image enhancement described herein is unavailable in the presently available methods in the technological field of endeavor pertaining to digital image enhancement. A method of an embodiment described herein, when implemented to execute on a device or data processing system, comprises substantial advancement of the functionality of that device or data processing system in weighting pixels of an image according to an uncertainty map for a region of the image, and the weighted pixels for more than one image averaged together to create a composite image that includes the more-certain parts of each individual image. Further, based on the results of an enhancement metric corresponding to the quality of the composite image, an additional image obtained if necessary to further improve the quality of the composite image.

The illustrative embodiments are described with respect to certain types of images, structures, uncertainties, maps, weights, thresholds, measurements, devices, data processing systems, environments, components, and applications only as examples. Any specific manifestations of these and other similar artifacts are not intended to be limiting to the invention. Any suitable manifestation of these and other similar artifacts can be selected within the scope of the illustrative embodiments.

Furthermore, the illustrative embodiments may be implemented with respect to any type of data, data source, or access to a data source over a data network. Any type of data storage device may provide the data to an embodiment of the invention, either locally at a data processing system or over a data network, within the scope of the invention. Where an embodiment is described using a mobile device, any type of data storage device suitable for use with the mobile device may provide the data to such embodiment, either locally at the mobile device or over a data network, within the scope of the illustrative embodiments.

The illustrative embodiments are described using specific code, designs, architectures, protocols, layouts, schematics, and tools only as examples and are not limiting to the illustrative embodiments. Furthermore, the illustrative embodiments are described in some instances using particular software, tools, and data processing environments only as an example for the clarity of the description. The illustrative embodiments may be used in conjunction with other comparable or similarly purposed structures, systems, applications, or architectures. For example, other comparable mobile devices, structures, systems, applications, or architectures therefor, may be used in conjunction with such embodiment of the invention within the scope of the invention. An illustrative embodiment may be implemented in hardware, software, or a combination thereof.

The examples in this disclosure are used only for the clarity of the description and are not limiting to the illustrative embodiments. Additional data, operations, actions, tasks, activities, and manipulations will be conceivable from this disclosure and the same are contemplated within the scope of the illustrative embodiments.

Any advantages listed herein are only examples and are not intended to be limiting to the illustrative embodiments. Additional or different advantages may be realized by specific illustrative embodiments. Furthermore, a particular illustrative embodiment may have some, all, or none of the advantages listed above.

Figure 2:
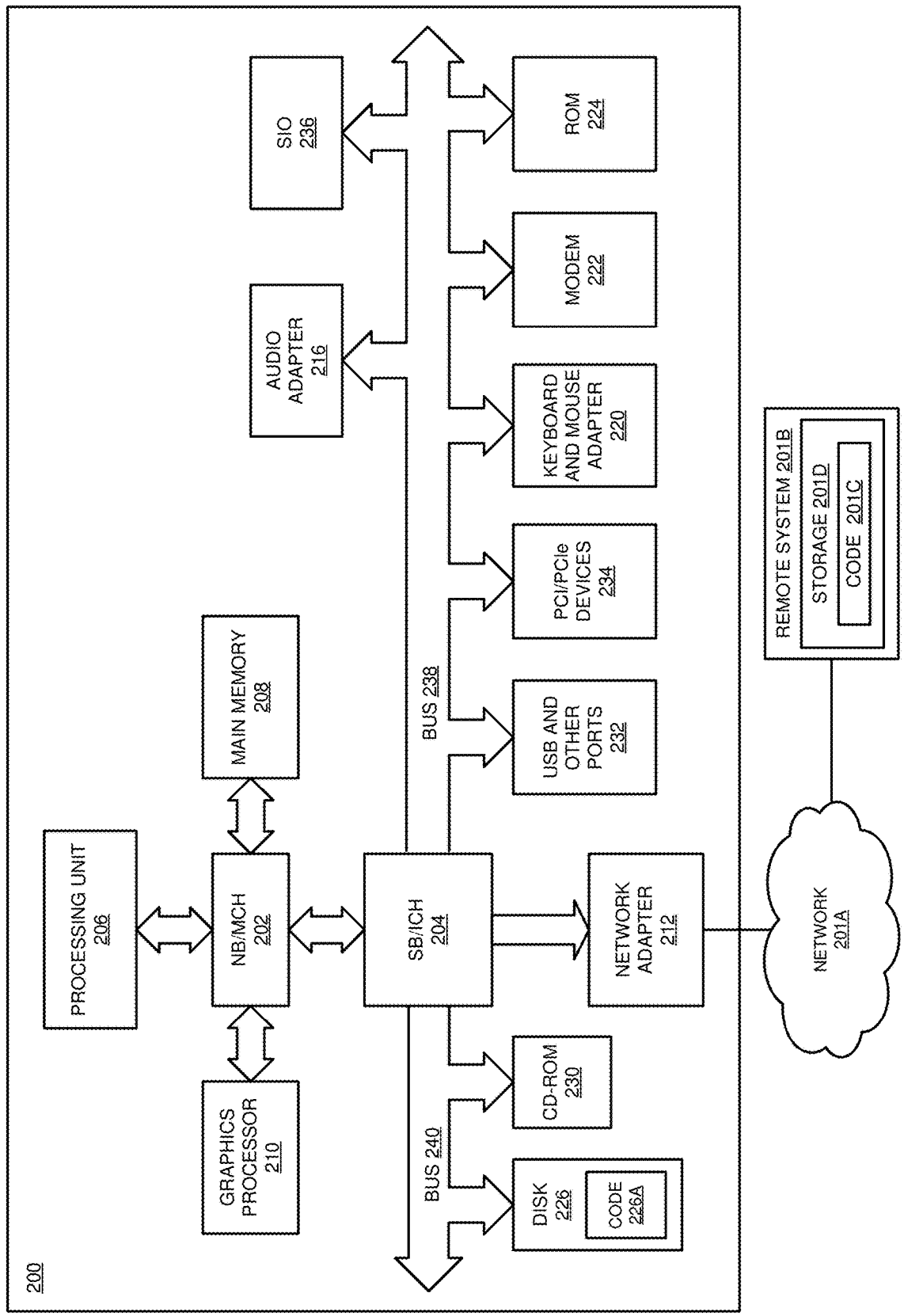
FIG. 2 depicts a block diagram of a data processing system in which illustrative embodiments may be implemented.

With reference to the figures and in particular with reference to FIGS. 1 and 2, these figures are example diagrams of data processing environments in which illustrative embodiments may be implemented. FIGS. 1 and 2 are only examples and are not intended to assert or imply any limitation with regard to the environments in which different embodiments may be implemented. A particular implementation may make many modifications to the depicted environments based on the following description.

FIG. 1 depicts a block diagram of a network of data processing systems in which illustrative embodiments may be implemented. Data processing environment 100 is a network of computers in which the illustrative embodiments may be implemented. Data processing environment 100 includes network 102. Network 102 is the medium used to provide communications links between various devices and computers connected together within data processing environment 100. Network 102 may include connections, such as wire, wireless communication links, or fiber optic cables.

Clients or servers are only example roles of certain data processing systems connected to network 102 and are not intended to exclude other configurations or roles for these data processing systems. Server 104 and server 106 couple to network 102 along with storage unit 108. Software applications may execute on any computer in data processing environment 100. Clients 110, 112, and 114 are also coupled to network 102. A data processing system, such as server 104 or 106, or client 110, 112, or 114 may contain data and may have software applications or software tools executing thereon.

Only as an example, and without implying any limitation to such architecture, FIG. 1 depicts certain components that are usable in an example implementation of an embodiment. For example, servers 104 and 106, and clients 110, 112, 114, are depicted as servers and clients only as example and not to imply a limitation to a client-server architecture. As another example, an embodiment can be distributed across several data processing systems and a data network as shown, whereas another embodiment can be implemented on a single data processing system within the scope of the illustrative embodiments. Data processing systems 104, 106, 110, 112, and 114 also represent example nodes in a cluster, partitions, and other configurations suitable for implementing an embodiment.

Device 132 is an example of a device described herein. For example, device 132 can take the form of a smartphone, a tablet computer, a laptop computer, client 110 in a stationary or a portable form, a wearable computing device, or any other suitable device. Any software application described as executing in another data processing system in FIG. 1 can be configured to execute in device 132 in a similar manner. Any data or information stored or produced in another data processing system in FIG. 1 can be configured to be stored or produced in device 132 in a similar manner.

Application 105 implements an embodiment described herein. Application 105 can execute in any of servers 104 and 106, clients 110, 112, and 114, and device 132. Application 105 receives image data from any suitable source, and stores the image data, for example in storage unit 108.

Servers 104 and 106, storage unit 108, and clients 110, 112, and 114, and device 132 may couple to network 102 using wired connections, wireless communication protocols, or other suitable data connectivity. Clients 110, 112, and 114 may be, for example, personal computers or network computers.

In the depicted example, server 104 may provide data, such as boot files, operating system images, and applications to clients 110, 112, and 114. Clients 110, 112, and 114 may be clients to server 104 in this example. Clients 110, 112, 114, or some combination thereof, may include their own data, boot files, operating system images, and applications. Data processing environment 100 may include additional servers, clients, and other devices that are not shown.

In the depicted example, data processing environment 100 may be the Internet. Network 102 may represent a collection of networks and gateways that use the Transmission Control Protocol/Internet Protocol (TCP/IP) and other protocols to communicate with one another. At the heart of the Internet is a backbone of data communication links between major nodes or host computers, including thousands of commercial, governmental, educational, and other computer systems that route data and messages. Of course, data processing environment 100 also may be implemented as a number of different types of networks, such as for example, an intranet, a local area network (LAN), or a wide area network (WAN). FIG. 1 is intended as an example, and not as an architectural limitation for the different illustrative embodiments.

Among other uses, data processing environment 100 may be used for implementing a client-server environment in which the illustrative embodiments may be implemented. A client-server environment enables software applications and data to be distributed across a network such that an application functions by using the interactivity between a client data processing system and a server data processing system. Data processing environment 100 may also employ a service oriented architecture where interoperable software components distributed across a network may be packaged together as coherent business applications. Data processing environment 100 may also take the form of a cloud, and employ a cloud computing model of service delivery for enabling convenient, on-demand network access to a shared pool of configurable computing resources (e.g. networks, network bandwidth, servers, processing, memory, storage, applications, virtual machines, and services) that can be rapidly provisioned and released with minimal management effort or interaction with a provider of the service.

With reference to FIG. 2, this figure depicts a block diagram of a data processing system in which illustrative embodiments may be implemented. Data processing system 200 is an example of a computer, such as servers 104 and 106, or clients 110, 112, and 114 in FIG. 1, or another type of device in which computer usable program code or instructions implementing the processes may be located for the illustrative embodiments.

Data processing system 200 is also representative of a data processing system or a configuration therein, such as data processing system 132 in FIG. 1 in which computer usable program code or instructions implementing the processes of the illustrative embodiments may be located. Data processing system 200 is described as a computer only as an example, without being limited thereto. Implementations in the form of other devices, such as device 132 in FIG. 1, may modify data processing system 200, such as by adding a touch interface, and even eliminate certain depicted components from data processing system 200 without departing from the general description of the operations and functions of data processing system 200 described herein.

In the depicted example, data processing system 200 employs a hub architecture including North Bridge and memory controller hub (NB/MCH) 202 and South Bridge and input/output (I/O) controller hub (SB/ICH) 204. Processing unit 206, main memory 208, and graphics processor 210 are coupled to North Bridge and memory controller hub (NB/MCH) 202. Processing unit 206 may contain one or more processors and may be implemented using one or more heterogeneous processor systems. Processing unit 206 may be a multi-core processor. Graphics processor 210 may be coupled to NB/MCH 202 through an accelerated graphics port (AGP) in certain implementations.

In the depicted example, local area network (LAN) adapter 212 is coupled to South Bridge and I/O controller hub (SB/ICH) 204. Audio adapter 216, keyboard and mouse adapter 220, modem 222, read only memory (ROM) 224, universal serial bus (USB) and other ports 232, and PCI/PCIe devices 234 are coupled to South Bridge and I/O controller hub 204 through bus 238. Hard disk drive (HDD) or solid-state drive (SSD) 226 and CD-ROM 230 are coupled to South Bridge and I/O controller hub 204 through bus 240. PCI/PCIe devices 234 may include, for example, Ethernet adapters, add-in cards, and PC cards for notebook computers. PCI uses a card bus controller, while PCIe does not. ROM 224 may be, for example, a flash binary input/output system (BIOS). Hard disk drive 226 and CD-ROM 230 may use, for example, an integrated drive electronics (IDE), serial advanced technology attachment (SATA) interface, or variants such as external-SATA (eSATA) and micro-SATA (mSATA). A super I/O (SIO) device 236 may be coupled to South Bridge and I/O controller hub (SB/ICH) 204 through bus 238.

Memories, such as main memory 208, ROM 224, or flash memory (not shown), are some examples of computer usable storage devices. Hard disk drive or solid state drive 226, CD-ROM 230, and other similarly usable devices are some examples of computer usable storage devices including a computer usable storage medium.

An operating system runs on processing unit 206. The operating system coordinates and provides control of various components within data processing system 200 in FIG. 2. The operating system may be a commercially available operating system for any type of computing platform, including but not limited to server systems, personal computers, and mobile devices. An object oriented or other type of programming system may operate in conjunction with the operating system and provide calls to the operating system from programs or applications executing on data processing system 200.

Instructions for the operating system, the object-oriented programming system, and applications or programs, such as application 105 in FIG. 1, are located on storage devices, such as in the form of code 226A on hard disk drive 226, and may be loaded into at least one of one or more memories, such as main memory 208, for execution by processing unit 206. The processes of the illustrative embodiments may be performed by processing unit 206 using computer implemented instructions, which may be located in a memory, such as, for example, main memory 208, read only memory 224, or in one or more peripheral devices.

Furthermore, in one case, code 226A may be downloaded over network 201A from remote system 201B, where similar code 201C is stored on a storage device 201D. in another case, code 226A may be downloaded over network 201A to remote system 201B, where downloaded code 201C is stored on a storage device 201D.

The hardware in FIGS. 1-2 may vary depending on the implementation. Other internal hardware or peripheral devices, such as flash memory, equivalent non-volatile memory, or optical disk drives and the like, may be used in addition to or in place of the hardware depicted in FIGS. 1-2. In addition, the processes of the illustrative embodiments may be applied to a multiprocessor data processing system.

In some illustrative examples, data processing system 200 may be a personal digital assistant (PDA), which is generally configured with flash memory to provide non-volatile memory for storing operating system files and/or user-generated data. A bus system may comprise one or more buses, such as a system bus, an I/O bus, and a PCI bus. Of course, the bus system may be implemented using any type of communications fabric or architecture that provides for a transfer of data between different components or devices attached to the fabric or architecture.

A communications unit may include one or more devices used to transmit and receive data, such as a modem or a network adapter. A memory may be, for example, main memory 208 or a cache, such as the cache found in North Bridge and memory controller hub 202. A processing unit may include one or more processors or CPUs.

The depicted examples in FIGS. 1-2 and above-described examples are not meant to imply architectural limitations. For example, data processing system 200 also may be a tablet computer, laptop computer, or telephone device in addition to taking the form of a mobile or wearable device.

Where a computer or data processing system is described as a virtual machine, a virtual device, or a virtual component, the virtual machine, virtual device, or the virtual component operates in the manner of data processing system 200 using virtualized manifestation of some or all components depicted in data processing system 200. For example, in a virtual machine, virtual device, or virtual component, processing unit 206 is manifested as a virtualized instance of all or some number of hardware processing units 206 available in a host data processing system, main memory 208 is manifested as a virtualized instance of all or some portion of main memory 208 that may be available in the host data processing system, and disk 226 is manifested as a virtualized instance of all or some portion of disk 226 that may be available in the host data processing system. The host data processing system in such cases is represented by data processing system 200.

Figure 3:
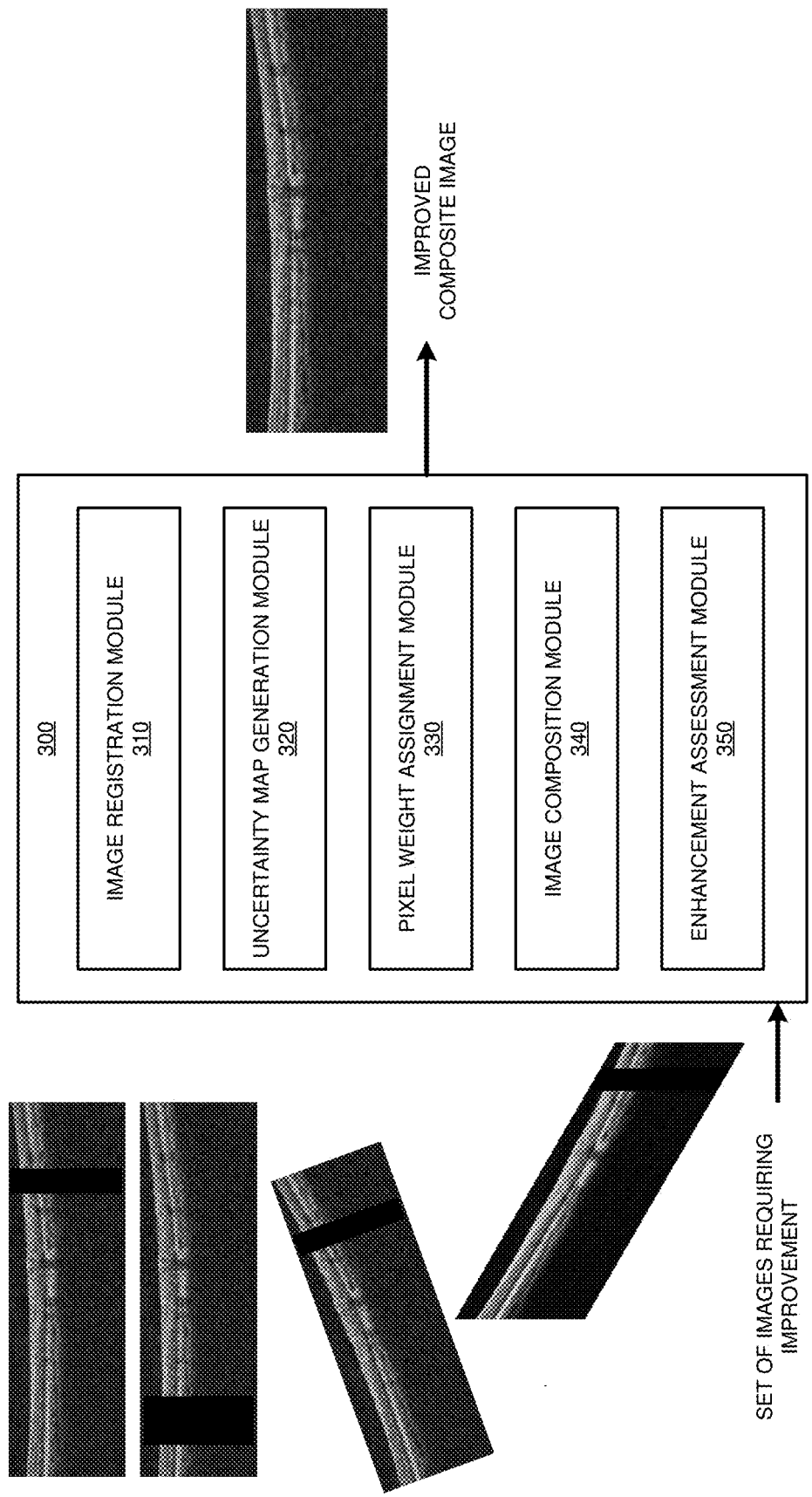
FIG. 3 depicts a block diagram of an example configuration for uncertainty region based image enhancement in accordance with an illustrative embodiment.

With reference to FIG. 3, this figure depicts a block diagram of an example configuration for uncertainty region based image enhancement in accordance with an illustrative embodiment. Application 300 is an example of application 105 in FIG. 1 and executes in any of servers 104 and 106, clients 110, 112, and 114, and device 132 in FIG. 1.

Image registration module 310 uses a prior-art registration process to register the received images. The registration process adjusts each image to conform to the alignment and size of a reference image of the known structure the embodiment is configured to process. As a result, during a later image composition process, pixels of different images being composited are located in the same relative position with respect to known structure within the subject of the images. In particular, if the received image is larger or smaller than the reference image, the received image is rescaled to match the reference image. If the received image is rotated with respect to the reference image, the received image is rotated to match the reference image. If the received image was taken from a point of view different from that of the reference image, the registration process performs a perspective transformation on the received image to match that of the reference image. If the received image was captured using a different intensity scale, or using a different color palette, from that of the reference image, the registration process converts the intensity scale or color palette of the received image to match that of the reference image. If the received image has a different depth of field from that of the reference image, the registration process adjusts the depth of field of the received image to match that of the reference image. The registration process also performs additional adjustments to the received image to ensure image alignment and sizing consistent with the reference image.

Uncertainty map generation module 320 uses a model to compute an uncertainty map corresponding to each image to be used in creating an enhanced image. The model identifies, within an image, the known structure the embodiment is configured to process. When the model identifies known structure at a location within an image, the model also produces a level of uncertainty associated with that identification at that location. The level of uncertainty is a number within a range, where the low end of the range (e.g. 0 percent) denotes a very low uncertainty (i.e. a very high confidence) in the model's identification, and the high end of the range (e.g. 100 percent) denotes a very high uncertainty (i.e. a very low confidence) in the model's identification. An uncertainty map maps these levels of uncertainty into a two-dimensional format, with a pixel of the uncertainty map having coordinates corresponding to an area within the image. A pixel of the uncertainty map has, as a value, the model's level of uncertainty for the corresponding image area.

Pixel weight assignment module 330 uses the uncertainty map corresponding to an image to compute a confidence weight. The confidence weight corresponds to the uncertainty level of a region of the image. This process of confidence weighting results in a weighted image.

In particular, pixel weight assignment module 330 converts an uncertainly level within an uncertainty map to a confidence weight using an inverse exponential function. In other words, the confidence weight of one pixel in the $i^{th}$ image is $$w_i = \frac{\exp(-U_i)}{\sum_{j=1}^{N} \exp(-U_j)},$$

where N is the total number of images being processed and $U_j$ is the uncertainty value for the corresponding pixel in the $i^{th}$ image. Thus, a higher weight is assigned to a pixel corresponding to a lower uncertainty value, and a lower weight is assigned to a pixel corresponding to a higher uncertainty value. In addition, in an embodiment all the weights assigned to a particular pixel, across all images being composited, sum to 1.

Image composition module 340 combines at least two weighted images to create a composite image, by computing a weighted average of corresponding pixels in each weighted image. Because the weighted images have been weighted according to uncertainty maps of each image, the composite image will include the least uncertain, or most certain, regions of each of the original images—thus combining the best parts of each source image.

Enhancement assessment module 350 computes an enhancement metric corresponding to the composite image. In particular, enhancement assessment module 350 averages together uncertainty maps used to create the composite image. Then, in one implementation, if at least a threshold number of pixels or regions in the resulting average uncertainty map are below a predetermined threshold, or at least a threshold number of pixels or regions of a portion of the average uncertainty map corresponding to a region of interest is below a predetermined threshold, the composite image is deemed to be sufficiently enhanced, and image processing may stop. The threshold number of pixels or regions can be, but need not necessarily be, all pixels, or all regions that are being considered in the processing.

Another implementation computes the enhancement metric R=1−(number of pixels with uncertainty value>T in a region of interest)/(total number of pixels in the region), where T is a predetermined threshold, is computed for a region of or the entire average uncertainty map. If the value of the resulting enhancement metric R is above a predetermined threshold, the composite image is deemed to be sufficiently enhanced, and image processing may stop.

If the value of the enhancement metric is not above a threshold, meaning that the composite image is not sufficiently improved, application 300 repeats the process of obtaining and registering an additional image, computing an uncertainty map corresponding to the additional image, computing a weighted image corresponding to the uncertainty map, and computing a new composite image from a set of weighted images including the new weighted image. If the new composite image has an enhancement metric value above a threshold, the process stops; otherwise application 300 iterates, processing an additional image until a composite image with a sufficient enhancement metric value is produced or a maximum number of iterations is reached. A sufficient enhancement metric value and a maximum number of iterations can be determined in cooperation with end users of particular types of images, to ensure that resulting composite images meet users' needs without requiring unrealistic numbers of images and associated imaging time and resources.

Figure 4:
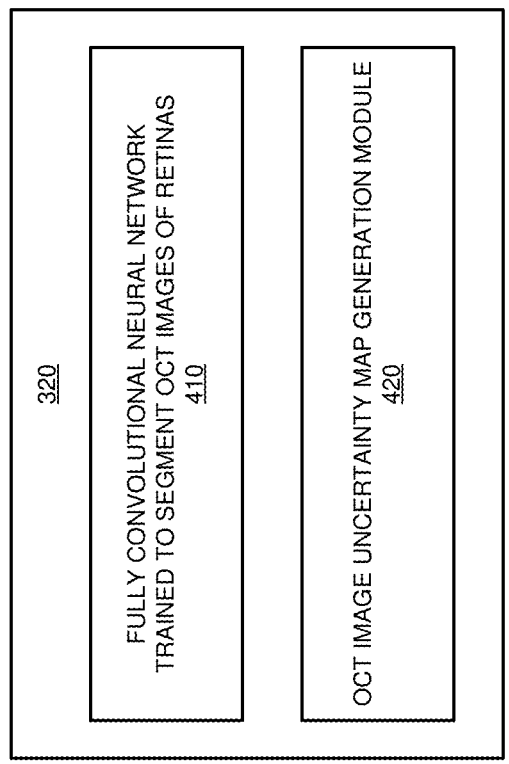
FIG. 4 depicts further detail of a block diagram of an example configuration for uncertainty region based image enhancement in accordance with an illustrative embodiment.

With reference to FIG. 4, this figure depicts further detail of a block diagram of an example configuration for uncertainty region based image enhancement in accordance with an illustrative embodiment. In particular, FIG. 4 provides more detail of block 320 in FIG. 3.

In an implementation configured for enhancing OCT images of retinas, the model used in uncertainty map generation module 320 in FIG. 3 is fully convolutional neural network 410. Neural network 410 is a fully convolutional neural network trained to identify retinal layers at a location within an image. Neural network 410 also produces a level of uncertainty associated with the retinal layer identification. Neural network 410 is an existing, already-trained model, and application 300 does not perform additional model training.

To determine an uncertainty value for a region of an image, OCT image uncertainty map generation module 420 applies the image region to neural network 410 and records the output of the neural network test phase. Then, module 420 removes a portion of the test phase, by temporarily assigning a lower weight to that portion. Over multiple iterations, module 420 reapplies the same region of the image as an input to neural network 410 and measures the new test phase output. The variance of the outputs over multiple test iterations determines an uncertainty level in the known structure identification for that region of the image, and the mean of the outputs is used as the final prediction of the structure in the image. In particular, if $y_1, y_2 \ldots y_T$ are T predictions made by the network then the prediction is computed as $$\mu = 1/T \sum_{i=1}^{T} y_i$$

and the uncertainty is computed as $$U = 1/T \sum_{i=1}^{T} (\mu - y_i)^2.$$

Module 420 can be configured to select a test phase portion for removal using any suitable pattern. The variance of the multiple outputs obtained from multiple test iterations determines an uncertainty level in the known structure identification for that region of the image.

Module 420 normalizes each uncertainty value within each uncertainty map to a common uncertainty range using a soft-max activation function. Normalizing the uncertainty values within each uncertainty map in this fashion ensures that each uncertainty map uses the same uncertainty scale and range. Normalizing the uncertainty values in this manner allows direct comparison of uncertainty maps.

Figure 5:
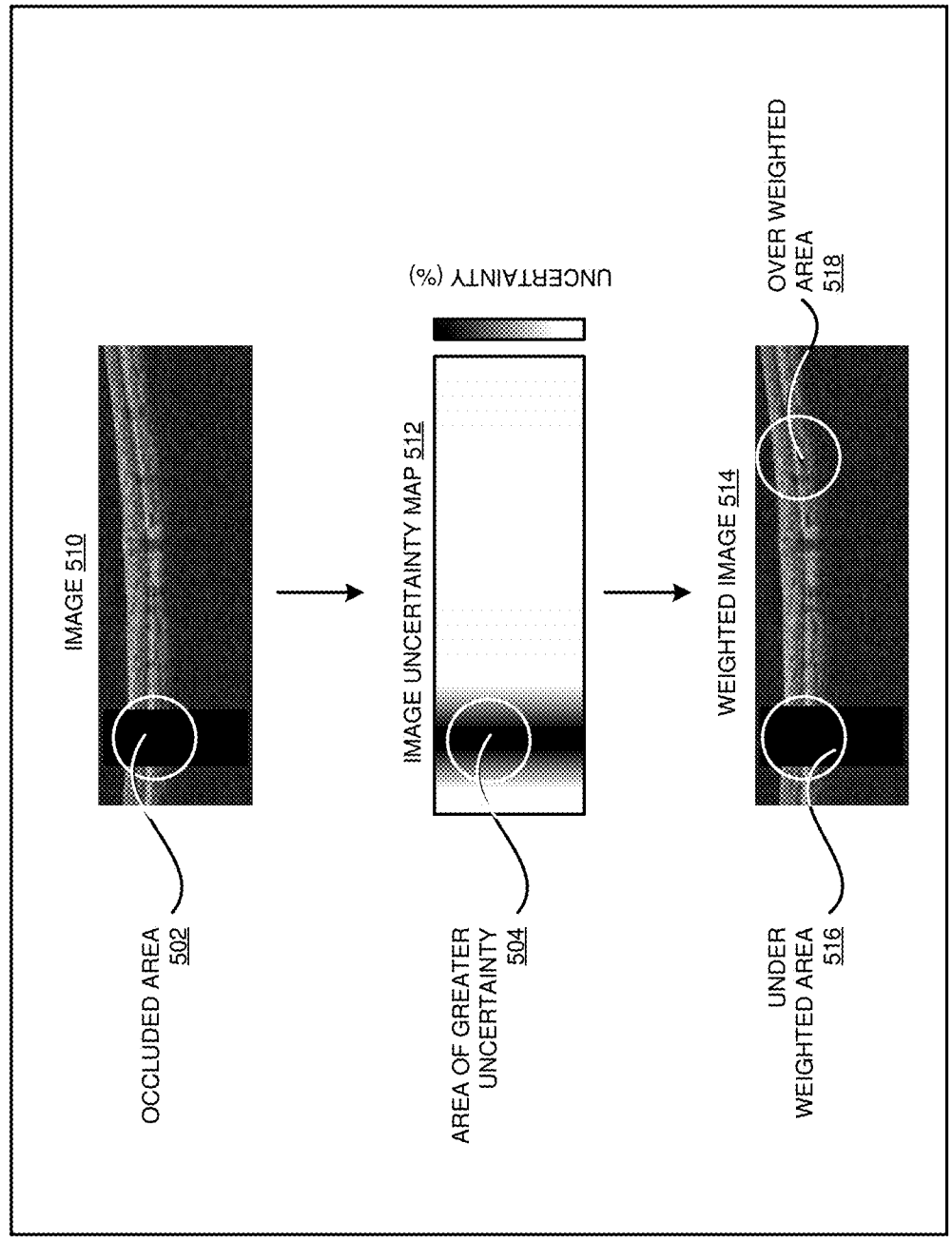
FIG. 5 depicts a an example of uncertainty region based image enhancement in accordance with an illustrative embodiment.

With reference to FIG. 5, this figure depicts a an example of uncertainty region based image enhancement in accordance with an illustrative embodiment. The examples in FIG. 5 are obtained using application 300 in FIG. 3.

Image 510 is a registered OCT image, including occluded area 502, that requires enhancement to fill in occluded area 502 and remove some speckle noise.

Application 300 uses a model, such as fully convolutional neural network 410 in FIG. 4, to compute image uncertainty map 512 corresponding to image 510. As shown by the uncertainty scale, image uncertainty map 512 includes area of greater uncertainty 504 corresponding to occluded area 502.

Application 300 uses image uncertainty map 512 to compute confidence weights corresponding to the uncertainty level of regions of image 510, resulting in weighted image 514. As a result, area of greater uncertainty 504 results in under weighted area 516, including pixels with a relatively lower weight than an average weighting, in weighted image 514. In contrast, a relatively less uncertain region of image 510, denoted by a lower uncertainty for that region in uncertainty map 512, will be relatively over-weighted in the resulting weighted image—for example, overweighted area 518, including pixels with a relatively higher weight than an average weighting. For example, most pixels in area 516 might have weights under 0.5 (on a 0-1 scale), while most pixels in area 518 might have weights above 0.5.

Figure 6:
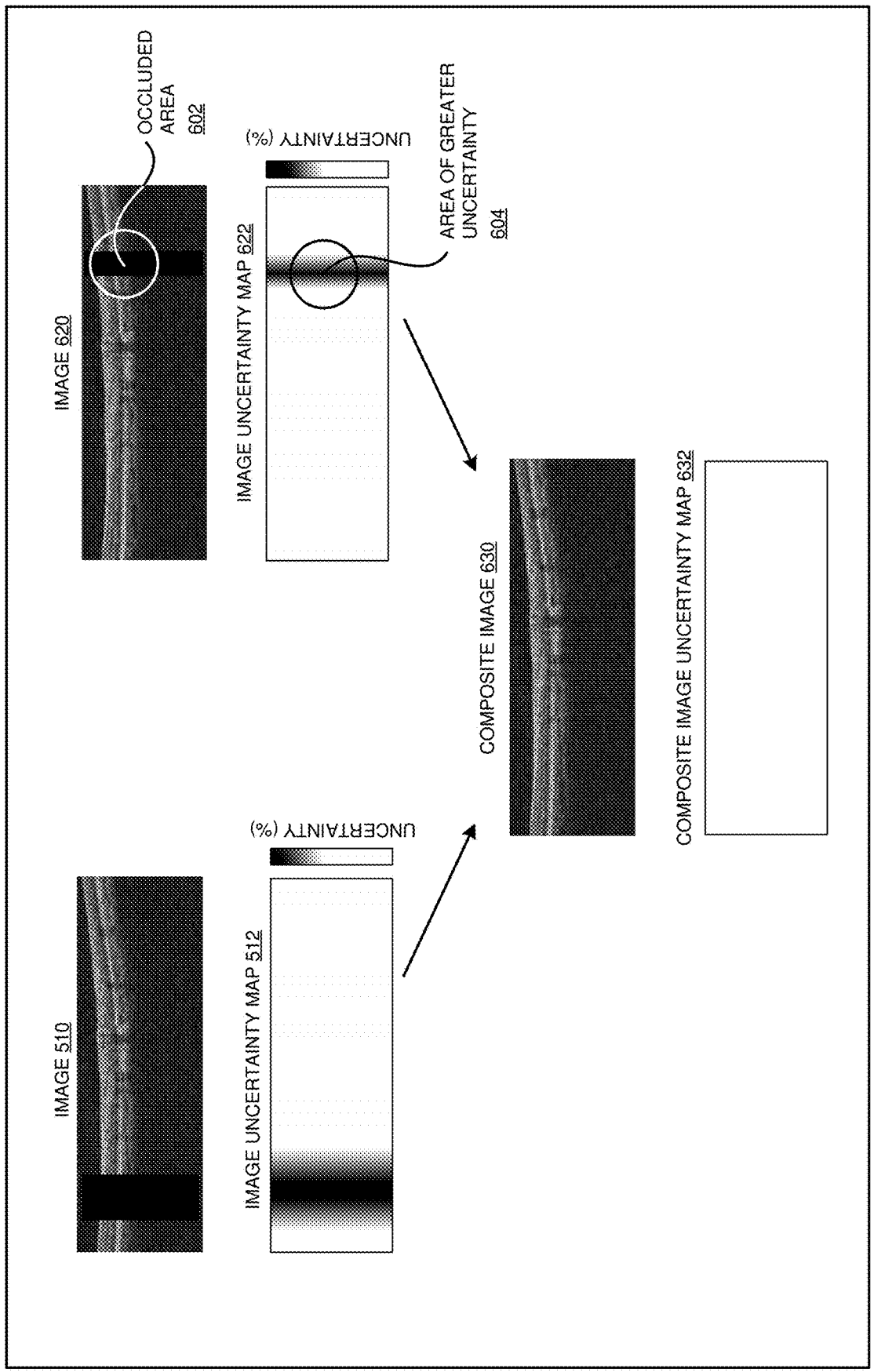
FIG. 6 depicts a continuation of an example of uncertainty region based image enhancement in accordance with an illustrative embodiment.

With reference to FIG. 6, this figure depicts a continuation of an example of uncertainty region based image enhancement in accordance with an illustrative embodiment. The examples in FIG. 6 are obtained using application 300 in FIG. 3. Image 510 and image uncertainty map 512 are the same as image 510 and image uncertainty map 512 in FIG. 5.

Image 620 is another registered OCT image of the same subject as image 510 that requires enhancement to fill in occluded area 602 and remove some speckle noise. Application 300 uses a model, such as fully convolutional neural network 410 in FIG. 4, to compute image uncertainty map 622 corresponding to image 620. As shown by the uncertainty scale, image uncertainty map 622 includes area of greater uncertainty 604 corresponding to occluded area 602. Application 300 uses image uncertainty map 622 to compute confidence weights corresponding to the uncertainty level of regions of image 620, including an under weighted area, including pixels with a relatively lower weight than an average weighting, corresponding to area 604 in image uncertainty map 622.

Application 300 computes a weighted average of corresponding pixels in two weighted images, corresponding to images 510 and 620, to create composite image 630. Because the weighted images have been weighted according to uncertainty maps of each image, the composite image will include the least uncertain, or most certain, regions of each of the original images—thus combining the best parts of each source image, as shown in composite image uncertainty map 632. Note that composite image 630 has the occluded areas of images 510 and 620 filled in, and composite image uncertainty map 632 does not include any areas of high uncertainty on the indicated uncertainty scale. Application 300 will use composite image uncertainty map 632 to compute an enhancement metric for composite image 630.

Figure 7:
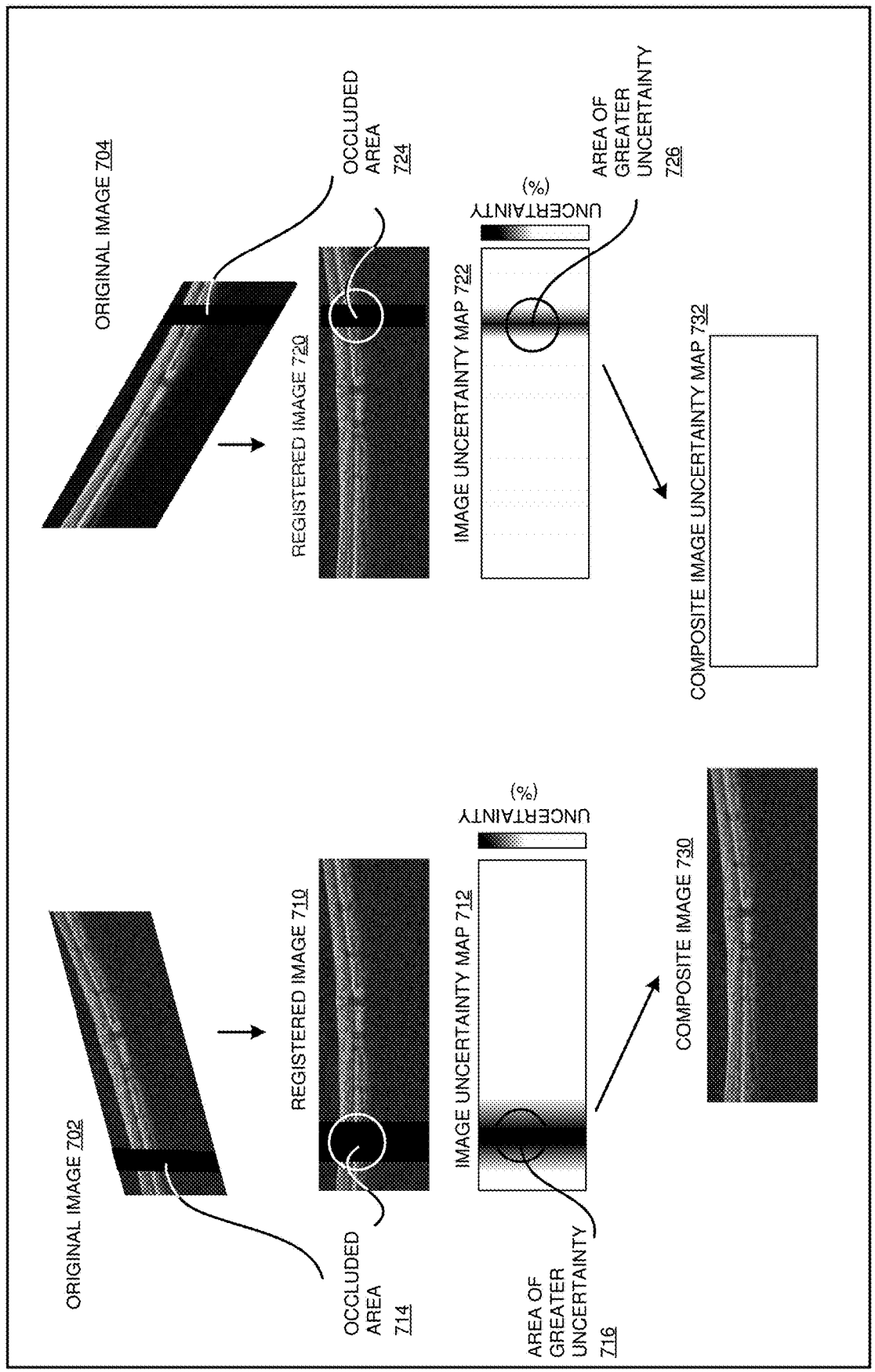
FIG. 7 depicts another example of uncertainty region based image enhancement in accordance with an illustrative embodiment.

With reference to FIG. 7, this figure depicts another example of uncertainty region based image enhancement in accordance with an illustrative embodiment. The examples in FIG. 7 are obtained using application 300 in FIG. 3.

Original OCT image 702 is an image captured from a different perspective than a reference image. Image 702 requires enhancement to fill in occluded area 714 and remove some speckle noise.

Application 300 uses a registration process to transform original image 702 into registered OCT image 710, also including occluded area 714. Then, application 300 uses a model, such as fully convolutional neural network 410 in FIG. 4, to compute image uncertainty map 712 corresponding to registered image 710. As shown by the uncertainty scale, image uncertainty map 712 includes area of greater uncertainty 716 corresponding to occluded area 714.

Original OCT image 704 is another image captured from a different perspective than both image 702 and a reference image. Image 704 also requires enhancement to fill in occluded area 724 and remove some speckle noise. Application 300 uses a registration process to transform original image 704 into registered OCT image 720, also including occluded area 724. Then, application 300 uses the same model as was used on image 710 to compute image uncertainty map 722 corresponding to registered image 720. As shown by the uncertainty scale, image uncertainty map 722 includes area of greater uncertainty 726 corresponding to occluded area 724.

Application 300 computes a weighted average of corresponding pixels in two weighted images, corresponding to registered images 710 and 720, to create composite image 730. Because the weighted images have been weighted according to uncertainty maps of each image, the composite image will include the least uncertain, or most certain, regions of each of the original images—thus combining the best parts of each source image, as shown in composite image uncertainty map 732. Note that composite image 730 has the occluded areas of images 710 and 720 filled in, and composite image uncertainty map 732 does not include any areas of high uncertainty on the indicated uncertainty scale. In addition, composite image 730 conforms to a standard orientation, scale, and perspective, unlike original images 702 and 704. Application 300 will use composite image uncertainty map 732 to compute an enhancement metric for composite image 730.

Figure 8:
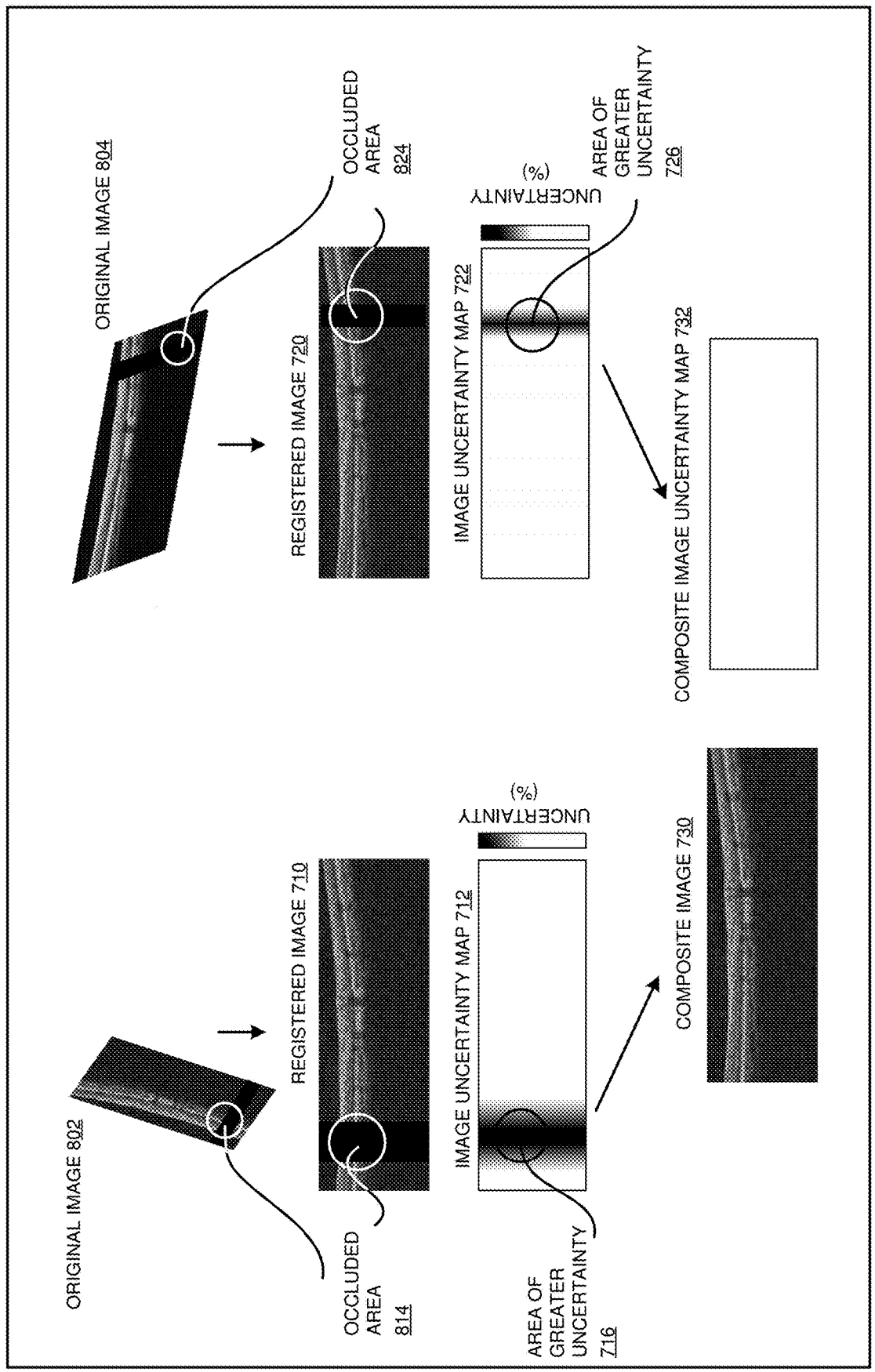
FIG. 8 depicts another example of uncertainty region based image enhancement in accordance with an illustrative embodiment.

With reference to FIG. 8, this figure depicts another example of uncertainty region based image enhancement in accordance with an illustrative embodiment. The examples in FIG. 8 are obtained using application 300 in FIG. 3. Registered images 710 and 720, image uncertainty maps 712 and 722, areas of greater uncertainty 716 and 726, composite image 730, and composite image uncertainty map 732 are the same as registered images 710 and 720, image uncertainty maps 712 and 722, areas of greater uncertainty 716 and 726, composite image 730, and composite image uncertainty map 732 in FIG. 7.

Original OCT image 802 is an image captured from a different perspective than a reference image, and is rotated with respect to the reference image. Image 802 requires enhancement to fill in occluded area 814 and remove some speckle noise.

Application 300 uses a registration process to transform original image 802 into registered OCT image 710, also including occluded area 814. Then, application 300 uses a model, such as fully convolutional neural network 410 in FIG. 4, to compute image uncertainty map 712 corresponding to registered image 710. As shown by the uncertainty scale, image uncertainty map 712 includes area of greater uncertainty 716 corresponding to occluded area 714.

Original OCT image 804 is another image captured from a different perspective than both image 802 and a reference image. In addition, image 804 is rotated differently from both image 802 and a reference image. Image 804 also requires enhancement to fill in occluded area 824 and remove some speckle noise.

Application 300 uses a registration process to transform original image 804 into registered OCT image 720, also including occluded area 724. Then, application 300 uses the same model as was used on image 710 to compute image uncertainty map 722 corresponding to registered image 720. As shown by the uncertainty scale, image uncertainty map 722 includes area of greater uncertainty 726 corresponding to occluded area 724.

Application 300 computes a weighted average of corresponding pixels in two weighted images, corresponding to registered images 710 and 720, to create composite image 730. Because the weighted images have been weighted according to uncertainty maps of each image, the composite image will include the least uncertain, or most certain, regions of each of the original images—thus combining the best parts of each source image, as shown in composite image uncertainty map 732. Note that composite image 730 has the occluded areas of images 710 and 720 filled in, and composite image uncertainty map 732 does not include any areas of high uncertainty on the indicated uncertainty scale. In addition, composite image 730 conforms to a standard orientation, scale, and perspective, unlike original images 802 and 804. Application 300 will use composite image uncertainty map 732 to compute an enhancement metric for composite image 730.

Figure 9:
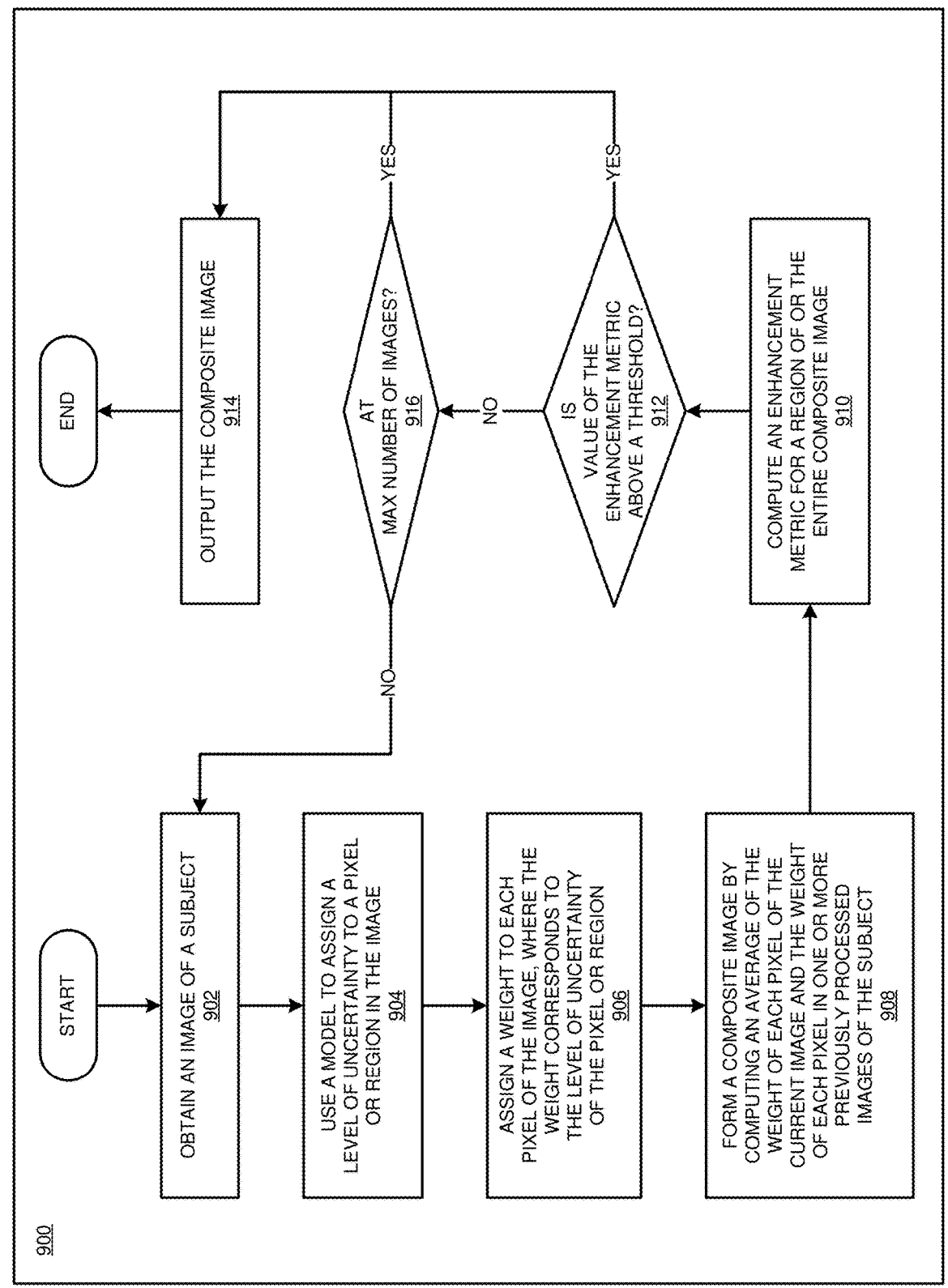
FIG. 9 depicts a flowchart of an example process for uncertainty region based image enhancement in accordance with an illustrative embodiment.

With reference to FIG. 9, this figure depicts a flowchart of an example process for uncertainty region based image enhancement in accordance with an illustrative embodiment. Process 900 can be implemented in application 300 in FIG. 3.

In block 902, the application obtains and registers an image of a subject. In block 904, the application uses a model, for example a fully convolutional neural network, to assign a level of uncertainty to a pixel or region in the image. In block 906, the application assigns a weight to each pixel of the image, where the weight corresponds to the level of uncertainty of the pixel or region. In block 908, the application forms a composite image by computing an average of the weight of each pixel of the current image with the weight of each pixel in one or more previously processed images of the subject. In block 910, the application computes an enhancement metric for a region of or the entire composite image. In block 912, the application checks whether the value of the enhancement metric is above a threshold. If yes ("YES" path of block 912), in block 914 the application outputs the composite image, then ends. Otherwise ("NO" path of block 912), in block 916 the application checks whether a maximum number of images has already been processed. If yes ("YES" path of block 916), in block 914 the application outputs the existing composite image, which has been enhanced as much as possible even if the enhancement metric threshold value has not been achieved. Otherwise ("NO" path of block 916), the application returns to block 902 to process another image of the subject.

Thus, a computer implemented method, system or apparatus, and computer program product are provided in the illustrative embodiments for uncertainty region based image enhancement and other related features, functions, or operations. Where an embodiment or a portion thereof is described with respect to a type of device, the computer implemented method, system or apparatus, the computer program product, or a portion thereof, are adapted or configured for use with a suitable and comparable manifestation of that type of device.

Where an embodiment is described as implemented in an application, the delivery of the application in a Software as a Service (SaaS) model is contemplated within the scope of the illustrative embodiments. In a SaaS model, the capability of the application implementing an embodiment is provided to a user by executing the application in a cloud infrastructure. The user can access the application using a variety of client devices through a thin client interface such as a web browser (e.g., web-based e-mail), or other light-weight client-applications. The user does not manage or control the underlying cloud infrastructure including the network, servers, operating systems, or the storage of the cloud infrastructure. In some cases, the user may not even manage or control the capabilities of the SaaS application. In some other cases, the SaaS implementation of the application may permit a possible exception of limited user-specific application configuration settings.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

What is claimed is:

1. A method comprising:
    generating, from a first image using a model, a first uncertainty map, wherein an uncertainty level of a location in the first uncertainty map corresponds to a detection of a known structure in a portion of the first image;
    generating, corresponding to the first uncertainty map, a first weighted image, the generating comprising assigning a first weight to a pixel of the first image, the first weight corresponding to the uncertainty level of a location in the first uncertainty map corresponding to the pixel;
    generating, from a second image using the model, a second uncertainty map, wherein an uncertainty level of a location in the second uncertainty map corresponds to a detection of a known structure in a portion of the second image;
    generating, corresponding to the second uncertainty map, a second weighted image, the generating comprising assigning a second weight to a pixel of the second image, the second weight corresponding to the uncertainty level of a location in the second uncertainty map corresponding to the pixel; and combining the first image and the second image to form a composite image, the first image participating in the composite image according to the first weighted image and the second image participating in the composite image according to the second weighted image.

2. The method of claim 1, further comprising:

computing an enhancement metric corresponding to the composite image;

generating, responsive to determining that a value of the enhancement metric is lower than a threshold, from a third image using the model, a third uncertainty map, wherein an uncertainty level of a location in the third uncertainty map corresponds to a detection of a known structure in a portion of the third image;

generating, corresponding to the third uncertainty map, a third weighted image, the generating comprising assigning a third weight to a pixel of the third image, the third weight corresponding to the uncertainty level of a location in the third uncertainty map corresponding to the pixel; and combining the first image, the second image, and the third image to form a second composite image, the first image participating in the composite image according to the first weighted image, the second image participating in the composite image according to the second weighted image, and the third image participating in the second composite image according to the third weighted image.

3. The method of claim 2, wherein computing an enhancement metric corresponding to the composite image comprises:

averaging, to form a composite uncertainty map, the first uncertainty map and the second uncertainty map;

computing the enhancement metric from the composite uncertainty map.

4. The method of claim 3, wherein computing the enhancement metric from the composite uncertainty map comprises:

setting, to a value denoting an acceptable level of uncertainty responsive to determining that each pixel in a region of the composite uncertainty map has an uncertainty level less than a threshold uncertainty level, the enhancement metric.

5. The method of claim 3, wherein computing the enhancement metric from the composite uncertainty map comprises:

setting, to a value denoting an unacceptable level of uncertainty responsive to determining that each pixel in a region of the composite uncertainty map has an uncertainty level greater than or equal to a threshold uncertainty level, the enhancement metric.

6. The method of claim 3, wherein computing the enhancement metric from the composite uncertainty map comprises:

setting, to a value computed by 1 minus a result of dividing a number of pixels having an uncertainty level greater than a threshold uncertainty level in a region of the composite uncertainty map by a total number of pixels in the region, the enhancement metric.

7. The method of claim 1, wherein combining the first image and the second image to form a composite image comprises:

identifying a first region of interest in the first image;

adjusting the first weighted image, the adjusting comprising setting the first weight to zero, the pixel corresponding to the first weight located in a region of the first image outside the first region of interest;

identifying a second region of interest in the second image; and adjusting the second weighted image, the adjusting comprising setting the second weight to zero, the pixel corresponding to the second weight located in a region of the second image outside the second region of interest; combining the adjusted first image and the adjusted second image to form an adjusted composite image, the adjusted first image participating in the composite image according to the first adjusted weighted image and the adjusted second image participating in the adjusted composite image according to the second adjusted weighted image.

8. The method of claim 7, further comprising:

computing an enhancement metric corresponding to the adjusted composite image, the enhancement metric computed for a region of the adjusted composite image corresponding to the first region of interest and the second region of interest;

generating, responsive to determining that a value of the enhancement metric is lower than a threshold, from a third image using the model, a third uncertainty map, wherein an uncertainty level of a location in the third uncertainty map corresponds to a detection of a known structure in a portion of the third image;

generating, corresponding to the third uncertainty map, a third weighted image, the generating comprising assigning a third weight to a pixel of the third image, the third weight corresponding to the uncertainty level of a location in the third uncertainty map corresponding to the pixel;

identifying a third region of interest in the third image; and adjusting the third weighted image, the adjusting comprising setting the third weight to zero, the pixel corresponding to the third weight located in a region of the third image outside the third region of interest; and combining the first adjusted image, the second adjusted image, and the third adjusted image to form a third composite image, the first adjusted image participating in the third composite image according to the first adjusted weighted image, the second adjusted image participating in the third composite image according to the second adjusted weighted image, and the third adjusted image participating in the third composite image according to the third adjusted weighted image.

9. The method of claim 1, wherein the first image and the second image were created at different times.

10. A computer usable program product comprising one or more computer-readable storage devices, and program instructions stored on at least one of the one or more storage devices, the stored program instructions comprising:

program instructions to generate, from a first image using a model, a first uncertainty map, wherein an uncertainty level of a location in the first uncertainty map corresponds to a detection of a known structure in a portion of the first image;

program instructions to generate, corresponding to the first uncertainty map, a first weighted image, the generating comprising assigning a first weight to a pixel of the first image, the first weight corresponding to the uncertainty level of a location in the first uncertainty map corresponding to the pixel;

program instructions to generate, from a second image using the model, a second uncertainty map, wherein an uncertainty level of a location in the second uncertainty map corresponds to a detection of a known structure in a portion of the second image;

program instructions to generate, corresponding to the second uncertainty map, a second weighted image, the generating comprising assigning a second weight to a pixel of the second image, the second weight corresponding to the uncertainty level of a location in the second uncertainty map corresponding to the pixel; and program instructions to combine the first image and the second image to form a composite image, the first image participating in the composite image according to the first weighted image and the second image participating in the composite image according to the second weighted image.

11. The computer usable program product of claim 10, further comprising:

program instructions to compute an enhancement metric corresponding to the composite image;

program instructions to generate, responsive to determining that a value of the enhancement metric is lower than a threshold, from a third image using the model, a third uncertainty map, wherein an uncertainty level of a location in the third uncertainty map corresponds to a detection of a known structure in a portion of the third image;

program instructions to generate, corresponding to the third uncertainty map, a third weighted image, the generating comprising assigning a third weight to a pixel of the third image, the third weight corresponding to the uncertainty level of a location in the third uncertainty map corresponding to the pixel; and program instructions to combine the first image, the second image, and the third image to form a second composite image, the first image participating in the composite image according to the first weighted image, the second image participating in the composite image according to the second weighted image, and the third image participating in the second composite image according to the third weighted image.

12. The computer usable program product of claim 11, wherein program instructions to compute an enhancement metric corresponding to the composite image comprises:

program instructions to average, to form a composite uncertainty map, the first uncertainty map and the second uncertainty map;

program instructions to compute the enhancement metric from the composite uncertainty map.

13. The computer usable program product of claim 12, wherein program instructions to compute the enhancement metric from the composite uncertainty map comprises:

program instructions to set, to a value denoting an acceptable level of uncertainty responsive to determining that each pixel in a region of the composite uncertainty map has an uncertainty level less than a threshold uncertainty level, the enhancement metric.

14. The computer usable program product of claim 12, wherein program instructions to compute the enhancement metric from the composite uncertainty map comprises:

program instructions to set, to a value denoting an unacceptable level of uncertainty responsive to determining that each pixel in a region of the composite uncertainty map has an uncertainty level greater than or equal to a threshold uncertainty level, the enhancement metric.

15. The computer usable program product of claim 12, wherein program instructions to compute the enhancement metric from the composite uncertainty map comprises:

program instructions to set, to a value computed by 1 minus a result of dividing a number of pixels having an uncertainty level greater than a threshold uncertainty level in a region of the composite uncertainty map by a total number of pixels in the region, the enhancement metric.

16. The computer usable program product of claim 10, wherein program instructions to combining the first image and the second image to form a composite image comprises:

program instructions to identify a first region of interest in the first image;

program instructions to adjust the first weighted image, the adjusting comprising setting the first weight to zero, the pixel corresponding to the first weight located in a region of the first image outside the first region of interest;

program instructions to identify a second region of interest in the second image; and program instructions to adjust the second weighted image, the adjusting comprising setting the second weight to zero, the pixel corresponding to the second weight located in a region of the second image outside the second region of interest;

program instructions to combine the adjusted first image and the adjusted second image to form an adjusted composite image, the adjusted first image participating in the composite image according to the first adjusted weighted image and the adjusted second image participating in the adjusted composite image according to the second adjusted weighted image.

17. The computer usable program product of claim 16, further comprising:

program instructions to compute an enhancement metric corresponding to the adjusted composite image, the enhancement metric computed for a region of the adjusted composite image corresponding to the first region of interest and the second region of interest;

program instructions to generate, responsive to determining that a value of the enhancement metric is lower than a threshold, from a third image using the model, a third uncertainty map, wherein an uncertainty level of a location in the third uncertainty map corresponds to a detection of a known structure in a portion of the third image;

program instructions to generate, corresponding to the third uncertainty map, a third weighted image, the generating comprising assigning a third weight to a pixel of the third image, the third weight corresponding to the uncertainty level of a location in the third uncertainty map corresponding to the pixel;

program instructions to identify a third region of interest in the third image; and program instructions to adjust the third weighted image, the adjusting comprising setting the third weight to zero, the pixel corresponding to the third weight located in a region of the third image outside the third region of interest; and program instructions to combine the first adjusted image, the second adjusted image, and the third adjusted image to form a third composite image, the first adjusted image participating in the third composite image according to the first adjusted weighted image, the second adjusted image participating in the third composite image according to the second adjusted weighted image, and the third adjusted image participating in the third composite image according to the third adjusted weighted image.

18. The computer usable program product of claim 10, wherein the computer usable code is stored in a computer readable storage device in a data processing system, and wherein the computer usable code is transferred over a network from a remote data processing system.

19. The computer usable program product of claim 10, wherein the computer usable code is stored in a computer readable storage device in a server data processing system, and wherein the computer usable code is downloaded over a network to a remote data processing system for use in a computer readable storage device associated with the remote data processing system.

20. A computer system comprising one or more processors, one or more computer-readable memories, and one or more computer-readable storage devices, and program instructions stored on at least one of the one or more storage devices for execution by at least one of the one or more processors via at least one of the one or more memories, the stored program instructions comprising:

program instructions to generate, from a first image using a model, a first uncertainty map, wherein an uncertainty level of a location in the first uncertainty map corresponds to a detection of a known structure in a portion of the first image;

program instructions to generate, corresponding to the first uncertainty map, a first weighted image, the generating comprising assigning a first weight to a pixel of the first image, the first weight corresponding to the uncertainty level of a location in the first uncertainty map corresponding to the pixel;

program instructions to generate, from a second image using the model, a second uncertainty map, wherein an uncertainty level of a location in the second uncertainty map corresponds to a detection of a known structure in a portion of the second image;

program instructions to generate, corresponding to the second uncertainty map, a second weighted image, the generating comprising assigning a second weight to a pixel of the second image, the second weight corresponding to the uncertainty level of a location in the second uncertainty map corresponding to the pixel; and program instructions to combine the first image and the second image to form a composite image, the first image participating in the composite image according to the first weighted image and the second image participating in the composite image according to the second weighted image.

* * * * *